United States Patent
Kantor

(10) Patent No.: US 10,603,221 B1
(45) Date of Patent: Mar. 31, 2020

(54) NONINVASIVE DEVICE AND METHOD FOR NECK LIFT

(71) Applicant: Van J. Kantor, Tarzana, CA (US)

(72) Inventor: Van J. Kantor, Tarzana, CA (US)

( * ) Notice: Subject to any disclaimer, the term of this patent is extended or adjusted under 35 U.S.C. 154(b) by 376 days.

(21) Appl. No.: 15/182,082

(22) Filed: Jun. 14, 2016

Related U.S. Application Data

(63) Continuation of application No. 13/345,567, filed on Jan. 6, 2012.

(60) Provisional application No. 61/430,305, filed on Jan. 6, 2011.

(51) Int. Cl.
*A61F 13/12* (2006.01)

(52) U.S. Cl.
CPC .................. *A61F 13/128* (2013.01)

(58) Field of Classification Search
CPC .............. A61F 5/08; A61F 2013/00374; A61F 2013/0119; A61F 2013/00127; A61F 2013/00131; A61F 2013/00148; A61F 13/122; A61F 13/128; A45D 44/22
See application file for complete search history.

(56) References Cited

U.S. PATENT DOCUMENTS

| | | |
|---|---|---|
| 1,195,117 A | 8/1916 | Spellerberg |
| 2,001,862 A | 5/1935 | Battey |
| 2,184,099 A | 12/1939 | Macdonald |
| 2,896,613 A | 7/1959 | Brown |
| 3,245,404 A | 4/1966 | Ritzcovan |
| 3,782,372 A | 1/1974 | Carlton |
| 4,653,483 A | 3/1987 | Clavin |
| 5,116,675 A | 5/1992 | Nash-Morgan |
| 5,476,478 A * | 12/1995 | Jackson ................ A45D 44/22 128/898 |
| 5,555,900 A * | 9/1996 | Rich .................... A45D 44/22 132/200 |
| 5,582,585 A | 12/1996 | Nash-Morgan |
| 5,755,232 A * | 5/1998 | Kalt ........................ A61F 5/08 128/845 |
| 6,045,470 A | 4/2000 | Wilcox et al. |
| 6,065,470 A * | 5/2000 | Van Cromvoirt ......... A61F 5/08 128/200.24 |
| 6,769,429 B1 | 8/2004 | Benetti |
| 6,897,281 B2 | 5/2005 | Lubnin et al. |
| 7,067,710 B1 | 6/2006 | Beaudry |

(Continued)

FOREIGN PATENT DOCUMENTS

WO   WO03105585 A1   12/2003

*Primary Examiner* — Alexander J Orkin
(74) *Attorney, Agent, or Firm* — Diedericks & Whitelaw, PLC.

(57) ABSTRACT

In an aspect, the device for stretching skin of a user's neck includes a stretchable body that extends along a first axis, a first end integrally connected to the stretchable body, and a second end integrally connected to the stretchable body. The device further includes an adhesion layer formed on one side of each of the first end and the second end for attaching the device to the skin of the user's neck. Each of the first end and the second end comprises a center part that is integrally formed with the stretchable elongate body, a first extension connected to the center part and extending along a second axis away from the center part, and a second extension connected to the center part opposite the first extension and extending along the second axis away from the center part and the first extension.

19 Claims, 9 Drawing Sheets

(56) References Cited

U.S. PATENT DOCUMENTS

| | | |
|---|---|---|
| 7,473,158 B2 | 1/2009 | Horton |
| 7,608,090 B2 | 10/2009 | Matsui |
| 7,806,749 B2 | 10/2010 | Horton |
| 7,993,182 B2 | 8/2011 | Horton et al. |
| 8,062,329 B2 | 11/2011 | Ierulli |
| 2001/0032645 A1* | 10/2001 | Cronk ................. A61F 5/08 128/200.24 |
| 2002/0000227 A1* | 1/2002 | Duyke ................. A61F 5/08 128/200.24 |
| 2002/0029011 A1 | 3/2002 | Dyer |
| 2003/0232069 A1 | 12/2003 | Horton |
| 2005/0042264 A1 | 2/2005 | Horton |
| 2006/0115519 A1* | 6/2006 | Matsui ............. A45D 44/22 424/443 |
| 2008/0097517 A1 | 4/2008 | Holmes et al. |
| 2008/0228217 A1* | 9/2008 | Friend ............. A45D 44/22 606/204.35 |
| 2009/0076542 A1 | 3/2009 | Jonn et al. |
| 2009/0100558 A1 | 4/2009 | Smith |
| 2009/0111357 A1 | 4/2009 | Horton |
| 2009/0149114 A1 | 6/2009 | Horton et al. |
| 2014/0100599 A1 | 4/2014 | Ha |

* cited by examiner

NONINVASIVE DEVICE AND METHOD FOR NECK LIFT

CROSS REFERENCE TO RELATED APPLICATION(S)

This application claims priority from U.S. Provisional Patent Application Ser. No. 61/430,305 filed Jan. 6, 2011, which is incorporated by reference herein.

BACKGROUND OF THE INVENTION

Field of the Invention

The present invention relates to a device and a method for providing a skin lift and in particular, a lift of excess skin around the front of the neck.

Description of the Related Art

For decades, women and men have tried to look younger using cosmetic surgery to get rid of or minimize wrinkles, folds and excess skin. Surgeons cut the skin and lift it, and remove excess skin. This process of course has all the risks of any surgery. Moreover, it requires time for doctor's appointments, the procedure itself, and recuperation time, as well as being costly.

There have been many attempts to improve looks without surgery. For example, U.S. Pat. Nos. 5,116,675 and 5,582,585 to Nash-Morgan disclose devices that are elastic and adhere to the neck to help lift the skin on the front of the neck. However, these products are somewhat cumbersome to manufacture, may involve the assembly of multiple different parts, and may be less comfortable and/or effective. Accordingly, a simpler, easier, more comfortable device to make and use is desirable.

SUMMARY

In an aspect, the device for stretching skin of a user's neck includes a stretchable body that extends along a first axis, a first end integrally connected to the stretchable body, and a second end integrally connected to the stretchable body. The device further includes an adhesion layer formed on one side of each of the first end and the second end for attaching the device to the skin of the user's neck. Each of the first end and the second end comprises a center part that is integrally formed with the stretchable elongate body, a first extension connected to the center part and extending along a second axis away from the center part, and a second extension connected to the center part opposite the first extension and extending along the second axis away from the center part and the first extension.

Each of the first end and the second end may be shaped to conform to and be placed in proximity to the curvature of the user's ear. Each of the first end and the second end may further include an edge that is distal to the stretchable body, and a mid-line disposed approximately midway between the edge and a connecting location between the stretchable body and a corresponding one of the first end and the second end. Each of the first extension and the second extension may expand in width, as measured along the second axis, from the connecting location to a location between the mid-line and the edge such that the corresponding one of the first end and the second end is shaped to conform to and be placed in proximity to the curvature of the user's ear.

Each of the first end and the second end may further include an edge that is distal to the stretchable body, and that defines a concave part that opens away from the stretchable body. The concave part may be configured to conform to and be placed in proximity to the curvature of the user's ear. The first extension and the second extension may each simultaneously extend away from the center part along the second axis and away from the body along the first axis.

The second extension may be longer than the first extension, and the second extension may be configured to extend below the user's ear. Each end further may further include a peelable layer divided into two parts such that one of the first extension and the second extension may be uncovered and attached to the user's skin while another one of the first extension and the second extension remains covered. In other embodiments, each end may further include a peelable layer divided into three parts such that the center part may be uncovered and attached to the user's skin while each of the first extension and the second extension remains covered.

The first extension and the second extension may be configured to adhere to the user's skin to resist lifting at the edges of the end of the device caused by a narrowing of the stretchable body when placed under tension. The stretchable body may be made of a urethane that is between 0.5 and 1.5 millimeters in thickness. The device may have an upright moisture vapor transmission rate 700 and 900 g/m$^2$/24 hours. The device may be configured to be adhered behind and in proximity to the user's ear before and stretched over the top of the user's head. The device may be configured to be adhered behind and in proximity to the user's ear and stretched behind the user's head.

DESCRIPTION OF THE PREFERRED EMBODIMENTS

Figure 1:
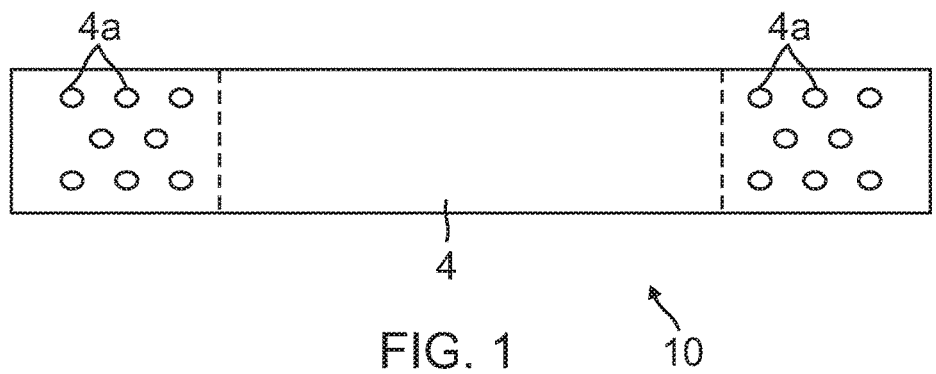
FIG. 1 is a plan view of a device in accordance with an embodiment of the invention.
Figure 2:
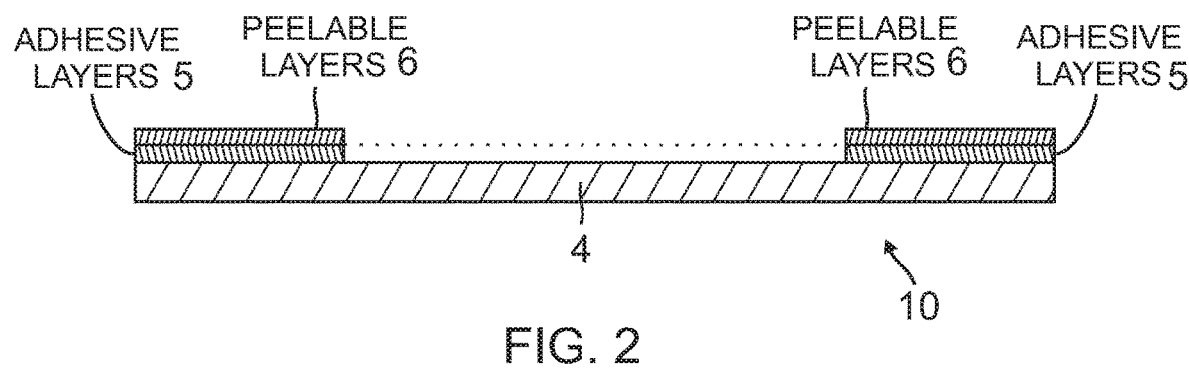
FIG. 2 is a sectional view of the device of FIG. 1.
Figure 3:
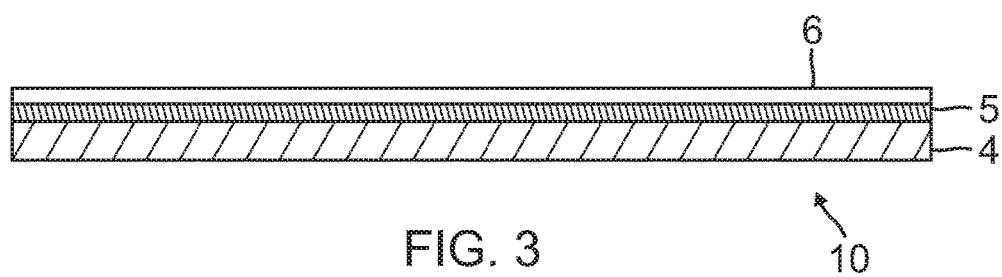
FIG. 3 is a sectional view of the device of FIG. 1 showing an alternative structure (to that of FIG. 2) for the adhesive and peelable layers.

As shown in FIGS. 1, and 2, a device 10 may have a generally elongated and rectangular body 4 having an adhesive layer 5 at each end of one main side of the body 4. The body 4 is preferably relatively thin and preferably is made of an elastic or resilient material that is skin-compatible. A peelable layer 6 that is preferably skin-compatible may cover adhesive layer 5. As shown in FIG. 2, the adhesive layer 5 and the peelable layer 6 may be disposed at each end of the body 4. In various embodiments, the adhesive layers 5 may each cover between 5% and 40% of the body 4. In other embodiments, the adhesive layers 5 may each cover between 15% and 30% of the body 4. As shown in FIG. 3, the adhesive layer 5 and the peelable layer 6 may extend across the length of the body 4. The body 4 is clear, although it could also come in various colors to match various skin and/or hair colors. In an embodiment, there are apertures or holes 4a (shown in FIG. 1) for venting in the body 4.

In multiple embodiments, the device 10 may be approximately six inches long, approximately one inch wide, and approximately 0.5 to 2 millimeters thick. The body 4 may be approximately 1 millimeter and the layer 6 may be approximately 1 millimeter thick. Approximately as used above may be, for example, plus or minus 10 percent or plus or minus 20 percent. Other variations may also work. For example, a thickness of three millimeters for the device 10 may work, such as a two millimeter thick body 4. Thinner materials may be less obtrusive.

In some embodiments designed to be worn around the back of the user's head, the device 10 may have a length between 1.0 inches and 10.0 inches. For example, the device 10 may be 6 inches long, or in other more preferred embodiments, between 1.5 and 3.0 inches long. In other preferred embodiments, the device 10 may be approximately 2 inches long, or in more preferred embodiments, approximately 2.5 inches long. In other embodiments designed for use over the top of a user's head, the device 10 may be approximately 7 inches long in more preferred embodiments. The device 10 may have different sizes to provide support for people with different sized heads or necks. Devices 2 shorter than the preferred ranges may be too tight to properly adhere or to provide a comfortable lifting effect, while devices 2 longer than the preferred size range may not provide enough tension to achieve a desired lifting effect. In multiple embodiments, the device 10 may be between 0.25 and 2 inches wide, and between 0.5 and 3 millimeters thick. In more preferred embodiments, the device 10 may be 0.75 inches wide.

A material used for the body 4 may be polyurethane e.g., a transparent polyurethane. The polyurethane may be single coated, and provide a fluid barrier that is breathable. The polyurethane may be supported by a polyethylene carrier and have an upright moisture vapor transmission rate (MVTR) of between 300 and 1300 $g/m^2/24$ hours, or in other more preferred embodiments, between 700 and 900 $g/m^2/24$ hours. In a more preferred embodiment, the upright MVTR may be approximately 800 $g/m^2/24$ hours. The inverted MVTR may be between 600 and 1600 $g/m^2/24$ hours, or in more preferred embodiments, between 1000 and 1200 $g/m^2/24$ hours. The elongation limit in more preferred embodiments may be approximately 400%, or in other embodiments, between 200% and 600%. The tensile strength limit may be between 5 lbs. and 23 lbs., or in other more preferred embodiments, between 11 and 17 lbs., or in even more preferred embodiments, approximately 14 lbs.

The adhesive may be a high grade medical adhesive, which may be used with hospital bandages. The adhesive may be designed to adhere even with moisture or some moisture from perspiration. For example, the adhesive may be a solvent based acrylic adhesive. The adhesive may be pressure sensitive and biologically inert, have a peel specification between 2.0 and 3.0 lbs./in, or in more preferred embodiments, approximately 2.5 lbs./in. In a more preferred embodiment, the adhesive may have a tack rating of approximately 700 gms, and a shear rating of approximately 30 minutes.

The manufacturing process of such a single device 10 is greatly simplified. For example, the resilient material may be formed in a web or long strip of the desired width and thickness. An adhesive layer 5 may be deposited or coated onto the appropriate portions of one main side at one or more manufacturing stations. The strip or web may then be moveable to one or more subsequent manufacturing stations where the peelable layer 6 is applied in one or more pieces. In another embodiment, the adhesive layer 6 may be a transfer adhesive that is adhered to the body 4 using a nip lamination procedure, in which a rotary press presses the peelable layer 6, the adhesive layer 4, and the body 4 together. The device 10 may then be cut to length and shape at a cutting station. In an embodiment, the body 4 in the portion on which adhesive layer 5 is disposed (and elsewhere as desired) may have perforations for assisting in breathability and avoiding excess moisture.

To use the device 10, a user may select an appropriate size device 10 appropriate for his/her neck size. The user's neck areas where the ends of the device 10 are to be adhered (e.g., behind and/or below the user's ears) may be cleaned using soap and water to remove dirt and oil, and may be further cleaned with an astringent such as rubbing alcohol before being allowed to dry to improve adhesive performance. The user may then peel off the peelable layer 6 at one end of the device 10, and may apply the end of the device 10 with the exposed adhesive layer 6 the neck. The adhesive layer 6 may be disposed on and pressed against the user's neck between 2 and 10 seconds to improve performance of a pressure-sensitive adhesive. The device 10 may be stretched before or after the first end of the device 10 is applied to the user's neck. Rubbing alcohol may assist with removal of the device 10 from the skin.

If the device 10 is configured to be disposed behind the user's head, the user may lift their hair out of the way to permit the device 10 to be stretched behind the user's head. If the device 10 is configured to be disposed over the top of the user's head, the user may create a part in their hairline over the top of their head to allow placement of the stretched device 10 over the top of the head. The user's hair may then be adjusted to conceal a stretched mid-portion of the device 10, either behind the head or over the top of the head. The user may then adhere the second end of the device 10 to the opposite side of the user's neck. The second end of the device 10 may be disposed behind and/or below the user's opposite ear.

In other embodiments, the user may select a device 10, and create a part in their hair to allow space for the device 10 to be stretched over the user's head. The user may then adhere one side of the device 10 to a first side of the user's neck, stretch the device 10 over the user's head, and then adhered to the other side of the user's neck. The user's hair may be used to conceal the device 10.

Figure 14:
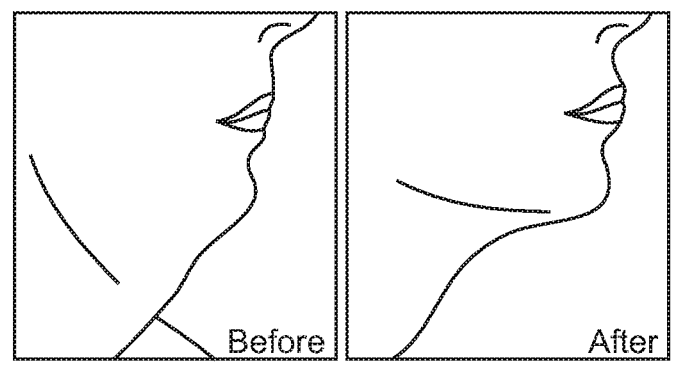
FIG. 14 is an illustration of potential before and after side views of a user's neck.

By applying the adhesive part of the strip to one side of the neck, then pulling the elastic strip across the back of the neck, and then attaching the strip by the adhesive part to the other side of the back of the neck, the resiliency or elasticity of the stretched strip will pull the neck's excess skin back and up, producing a tightened and smooth (or smoother) neck skin look like that on the right side of FIG. 14. The more the user stretches the strip before attaching the second end of the strip to the back of the neck, the more excess skin that can be pulled back. Caution should be used not to exceed the elastic limits of the strip, and not to create too much discomfort.

The exact amount of "stretch" in the device 10 when it is applied is up to the user, depending upon the user's desired comfort level and the user's desired improvement of skin appearance, and the desired length of time that the device 10 will be worn. The device 10 may be designed to be worn over the course of multiple hours (e.g., up to 6 to 8 hours, which may depend on the user's skin sensitivity and comfort). In an embodiment, the device may be removed while the user is sleeping to allow the adhesion areas of the skin to be rested.

Figure 4A:
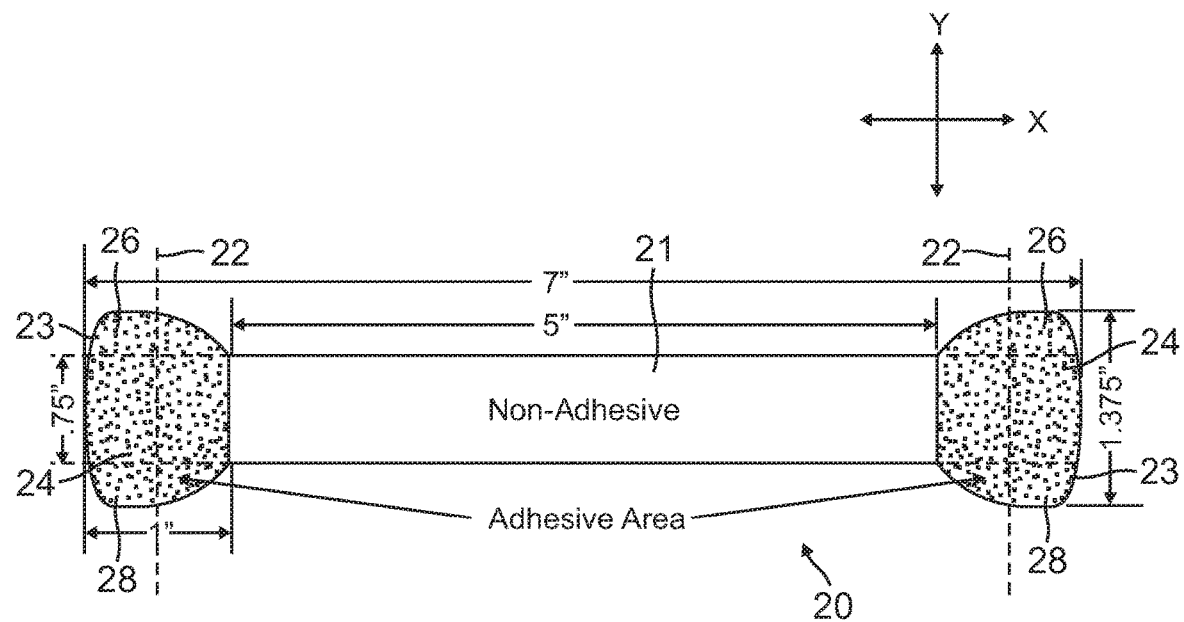
FIGS. 4A-4B are plan views of another embodiment of the device of FIG. 1.
Figure 4B:
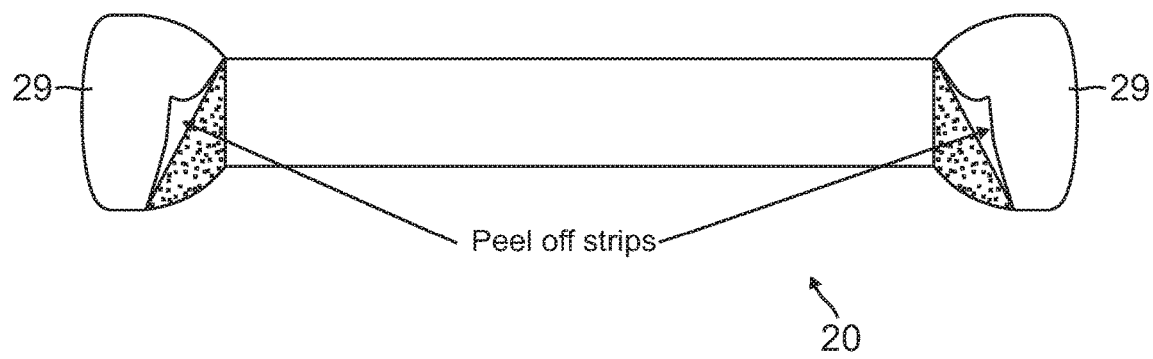

FIGS. 4A and 4B illustrate an embodiment of a device 20 that includes a body 21 and two ends, with each end having a center part 24, an edge 23 distal to the body 21, a first extension 26, and a second extension 28. The first extension 26 and the second extension 28 may form opposite sides of the end, and the center part 24 may have the same width as and be connected to the body 21. The body 21 may extend parallel to the X-axis. Each end may further include a mid-line 22 disposed approximately midway between the body 21 and the edge 23.

The length of the device 20 along the X-axis may be approximately 7 inches, or between 5 and 9 inches. The length of the body 21 along the X-axis may be between 3 and 7 inches, or approximately 5 inches. The length of each end along the X-axis may be between 0.5 and 2 inches, or approximately 1 inch. The width of the body 21 and the center parts 24 along the Y-axis may be between 0.5 and 2 inches, or approximately 0.75 inches. The width of the first extension 26 and the second extension 28 may each be approximately 0.3125, or between 0.1 and 0.5 inches along the Y-axis. The materials used for the device 20 may be similar to those of the device 10.

The first extension 26 and the second extension 28 may taper to the width of the body 21 where each end is connected to the body 21. For ends that are integrally formed with the body 21, each end may terminate at the edge of the corresponding adhesive layer. The first extension 26 and the second extension 28 may each extend in width along a Y-axis at the mid-line 22. The first extension 26 and the second extension 28 may continue to expand or remain constant in width between the mid-line and the edge 23 that is distal to the body 21. The corners of the edge 23 may be rounded. The first extension 26 and the second extension 28 may be formed such that a distal part of the end past the mid-line 22 is greater in width than a proximal part of the end as measured along the Y-axis.

Figure 5:
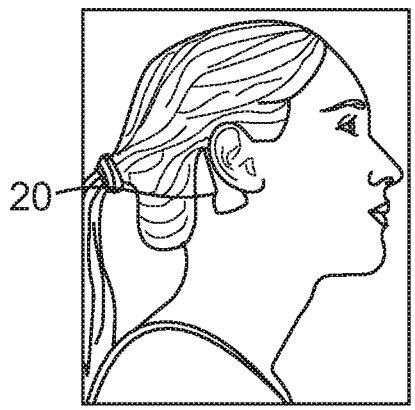
FIG. 5 is an illustration of the device of FIGS. 4A-4B being worn over the head of a user.
Figure 6:
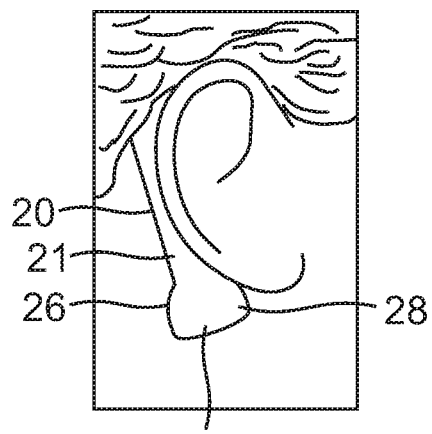
FIG. 6 is an illustration of placement of the device of FIGS. 4A-4B.

FIGS. 5 and 6 illustrate possible placement of the device 20 of FIGS. 4A and 4B on a user. As shown, the device 20 may be placed behind the ear of the user and stretched over the top of the user's head. The user's hair may be used to conceal the body 21.

One or more of the attributes described above may improve adhesion of the device 20 to the surface of the user's skin by reducing a likelihood of curling at the opposite sides of the end. In addition, the expanded width of the ends of the device 20 may provide increased control over the placement of the device on a user's skin. The tapering form of the proximal part of the ends of the device may allow the device to conform to and be placed in proximity to the curve of a user's ear, permitting the device 20 to be mounted at a location that may be more effective at tightening loose skin and may allow the device 20 to be more easily concealed behind a user's hair, ear, and/or earrings.

The overall dimensions and form of the device 20 may further provide a balance between tension effects on a user's skin, concealability, comfort, and/or reliability of adhesion.

When the device 20 is used, the body 21 may be stretched along the X-axis and may become narrower and/or curl around the X-axis. As the body 21 is placed under tensile stress, the ends of the device 20 that are adhered to a user's neck may be pulled parallel to the direction in which the device 20 has been stretched. The narrowing and/or curling of the body 21 may also cause portions of the adhered ends of the device 20 to experience Y-axis stress components and/or a Z-axis (e.g., an axis perpendicular to the X-axis and Y-axis) torsion. These affects may be greater at the edges of the body 21 than at the center of the width of the body 21 as measured along the Y-axis.

The width of the first extension 26 and the second extension 28 along the Y-axis may assist with resisting Y-axis linear and/or torsional stresses caused by the necking and/or curling of the body 21. The tapering of the proximal part of the end of the device 20 may assist with reducing a stress concentration at the junction between the device end and the body 21.

As shown in FIG. 4B, peelable layers 29 may cover the adhesive areas at the ends of the device 20. In other embodiments (not shown), the peelable layers 29 may be divided into 2, 3 or more parts to facilitate placement of the device 20. For example, the peelable layers 49 may be divided along the center line of the body 21 to permit one of the first extension 26 and the second extension 28 to be uncovered and adhered before the other one of the first extension 26 and the second extension is adhered. In another embodiment, the peelable layers 29 may be divided into three parts to separately cover the center part 24, the first extension 26, and the second extension 28. The section of the peelable layers 29 covering the center part 24 may be removed first to allow placement of the end of the device 20. The section of the peelable layers 29 covering one of the first extension 26 and the second extension 28 may then be removed to allow placement of the corresponding extension before the other extension is exposed and adhered to the user's skin.

Figure 7:
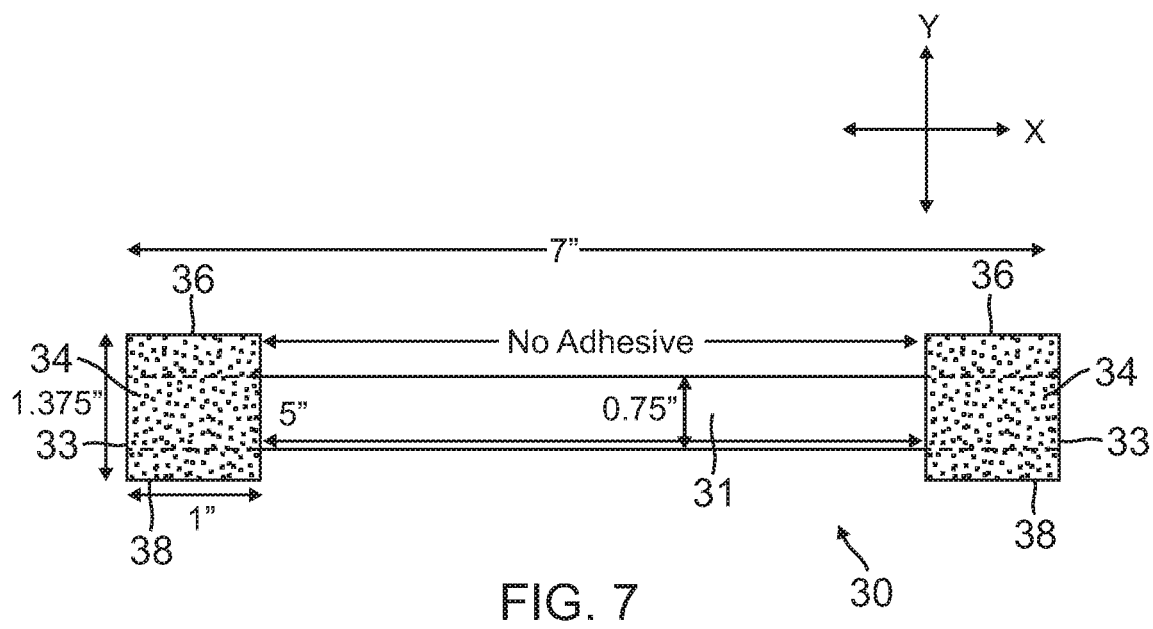
FIG. 7 is an illustration of another embodiment of the invention.

In the embodiment of FIG. 7, a device 30 includes a body 31 and two ends. Each end includes a center part 34, an edge 33 distal to the body 31, a first extension 36, and a second extension 38. The first extension 36 and the second extension 38 may form opposite sides of the end, and the center part 34 may have the same width as the body 31. The body 31 may extend parallel to the X-axis. The materials used for the device 30 may be similar to those of the device 10, 20.

The dimensions of the device 30 may be similar to the dimensions of the device 20, the primary difference being the rectangular form of the ends of the device 30. The overall dimensions and form of the device 30 may further provide a balance between tension effects on a user's skin, concealability, comfort, and/or reliability of adhesion.

Figure 8A:
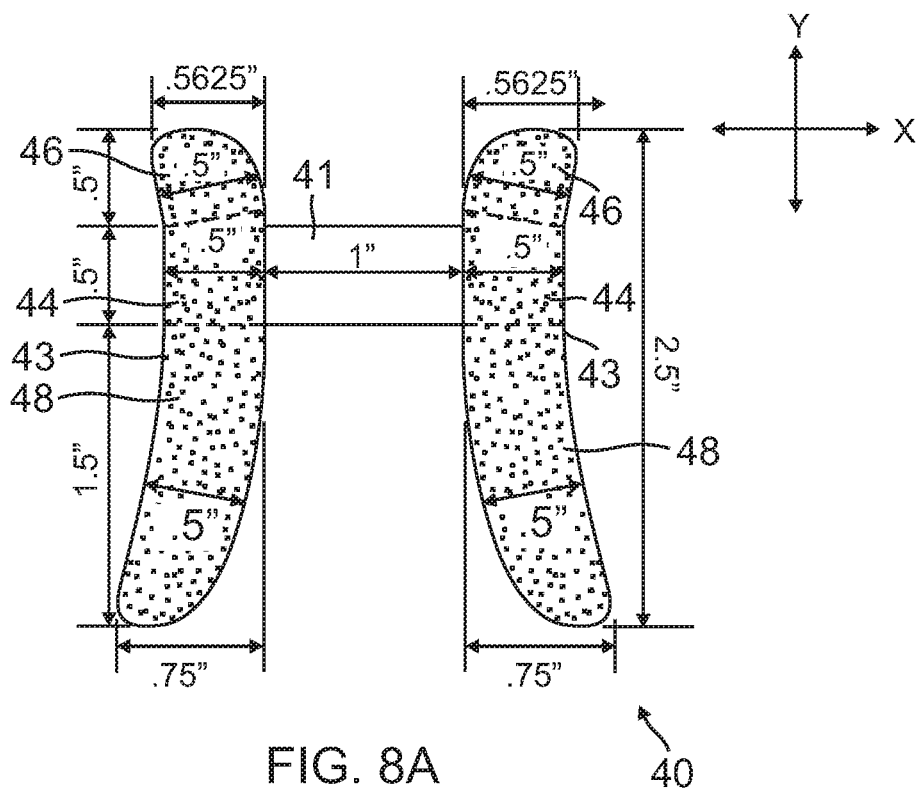
FIGS. 8A-8B are illustrations of another embodiment of the invention.
Figure 8B:
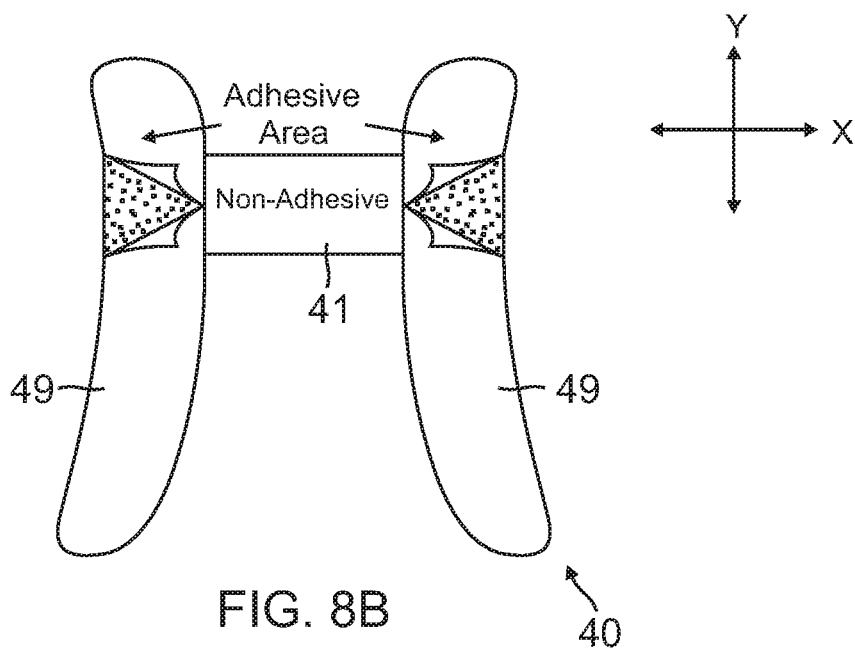

In the embodiment of FIGS. 8A and 8B, the device 40 may include a body 41 and two ends, with each end having a center part 44, an edge 43 distal to the body 41, a first extension 46, and a second extension 48. The first extension 46 and the second extension 48 may form opposite sides of the end, and the center part 44 may have the same width as and be connected to the body 41. The body 41 may extend parallel to the X-axis.

The length of the device 40 along the X-axis may be approximately 2.5 inches, or between 1.5 and 3.5 inches. The length of the body 41 along the X-axis may be between 0.25 and 1.75 inches, or approximately 1 inch. Each end as measured along the X-axis may be between 0.25 and 1.25 inches, or approximately 0.75 inches. The width of the body 41 and the center parts 44 along the Y-axis may be between 0.25 and 0.75 inches, or approximately 0.5 inches. The first extension 46 may have a width of approximately 0.5 inches, or between 0.25 and 0.75 inches in various embodiments. The first extension 46 may have a length of approximately 0.5 inches as measured along the Y-axis, or between 0.25 and 0.75 inches in various embodiments. The second extension 48 may have a width of approximately 0.5 inches, or between 0.25 and 0.75 inches in various embodiments. The second extension 48 may have a length of approximately 1.5 inches as measured along the Y-axis, or between 0.5 and 3 inches in various embodiments. The first extension 46 and the second extension 48 may each simultaneously extend away from the center part 44 along the Y-axis and away from the body 41 along the X-axis. The edge 43 may define a cavity that opens away from the body 41. The concave part may be configured to conform to and/or be placed in proximity to the user's ear. Each of the first extension 46 and the second extension 48 may have a substantially constant width (e.g., plus or minus 20% width) and a rounded end. The materials used for the device 40 may be similar to those of the device 10, 20, 30. The second extension 48 may be configured to extend around and below the user's ear.

Figure 9:
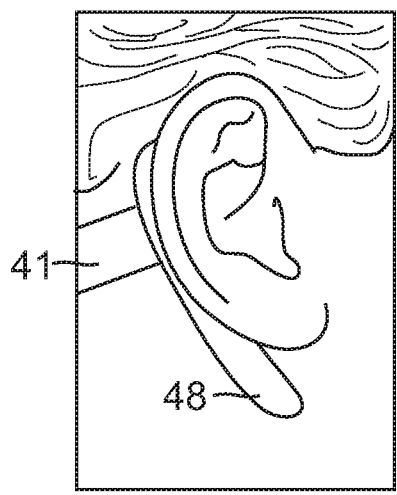
FIGS. 9 and 10 illustrate placement of the device of FIGS. 8A-8B.
Figure 10:
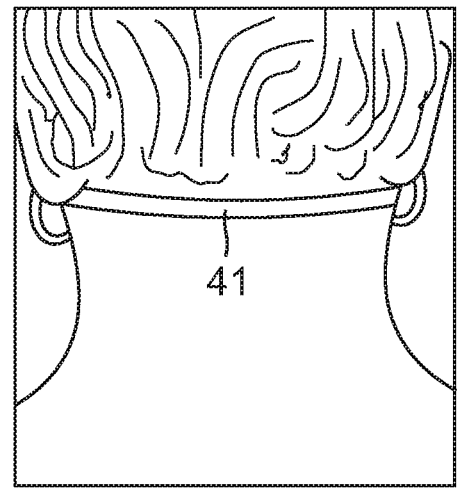
Figure 11A:
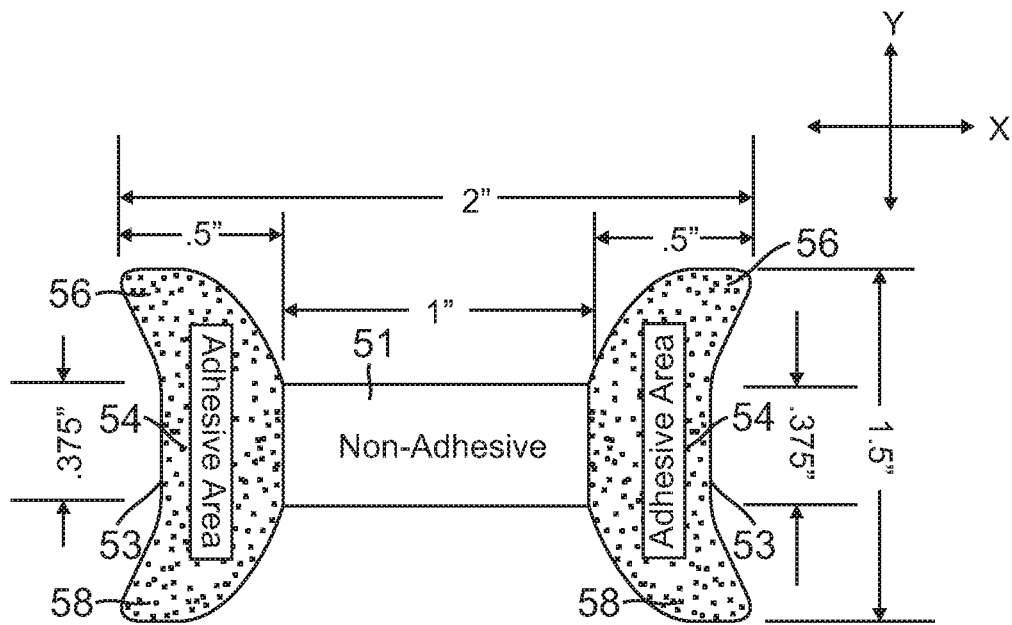
FIG. 11A-11B illustrates another embodiment of the invention.
Figure 11B:
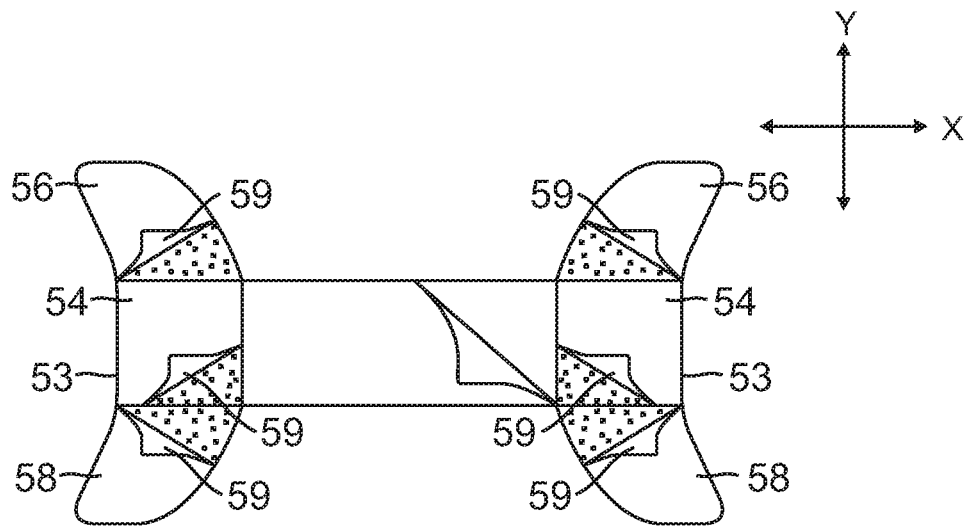

FIGS. 9 and 10 illustrate possible placement of the device 40 of FIGS. 8A and 8B on a user. As shown, the device 40 may be placed behind the ear of the user and stretched behind the user's head. The user's hair may be used to conceal the body 41.

One or more of the attributes described above may improve adhesion of the device 40 to the surface of the user's skin by reducing a likelihood of curling at the opposite sides of the end. In addition, the curvature of the edge 43 may permit the device 40 to be placed in closer proximity behind the user's ears. The greater length of the second extension 48 may permit the device 40 to apply tension across areas that may provide a better lifting effect than shorter extensions while remaining relatively unobtrusive.

When the device 40 is used, the body 41 may be stretched along the X-axis and may become narrower and/or curl around the X-axis. As the body 41 is placed under tensile stress, the ends of the device 40 that are adhered to a user's neck may be pulled parallel to the direction in which the device 40 has been stretched. The narrowing and/or curling of the body 41 may also cause portions of the adhered ends of the device 40 to experience Y-axis stress components and/or a Z-axis (e.g., an axis perpendicular to the X-axis and Y-axis) torsion. These affects may be greater at the edges of the body 41 than at the center of the width of the body 41 as measured along the Y-axis.

The asymmetrical lengths of the first extension 46 and the second extension 48, the angles at which the first extension 46 and second extension 48 extend, and/or the curvature of the edge 43 may assist with resisting Y-axis linear and/or torsional stresses caused by the necking and/or curling of the body 41.

As shown in FIG. 8B, peelable layers 49 may cover the adhesive areas at the ends of the device 40. In various embodiments, the peelable layers 49 may be divided into 2, 3 or more parts to facilitate placement of the device 40. For example, in FIG. 8B, the peelable layers 49 are divided along the center line of the body 41 to permit one of the first extension 46 and the second extension 48 to be uncovered and adhered before the other one of the first extension 46 and the second extension 48 is adhered. In another embodiment, the peelable layers 49 may be divided into three parts to separately cover the center part 44, the first extension 46, and the second extension 48. The section of the peelable layers 49 covering the center part 44 may be removed first to allow placement of the end of the device 40. The section of the peelable layers 49 covering one of the first extension 46 and the second extension 48 may then be removed to allow placement of the corresponding extension before the other extension is exposed and adhered to the user's skin.

In the embodiment of FIG. 10, a device 50 includes a body 51 and two ends, with each end having a center part 54, an edge 53 distal to the body 51, a first extension 56, and a second extension 58. The first extension 56 and the second extension 58 may form opposite sides of the end, and the center part 54 may have the same width as and be connected to the body 51. The body 51 may extend parallel to the X-axis. The materials used for the device 50 may be similar to those of the device 10, 20, 30, 40.

The form of the device 50 may be similar to the form of the device 40, the primary difference being that the first extension 56 and the second extension 58 are substantially similar rather than different. The overall dimensions and form of the device 50 may further provide a balance between tension effects on a user's skin, concealability, comfort, and/or reliability of adhesion.

The length of the device 50 along the X-axis may be approximately 2 inches, or between 1 and 3 inches. The length of the body 51 along the X-axis may be between 0.5 and 1.5 inches, or approximately 1 inch. Each end as measured along the X-axis may be between 0.25 and 1 inches, or approximately 0.5 inches. The width of the body 51 and the center parts 54 along the Y-axis may be between 0.25 and 0.75 inches, or approximately 0.375 inches. The first extension 56 and second extension 58 may each have a width that tapers from the base to the end of each extension. The first extension 56 and second extension 58 may each have a length of approximately 0.5625 inches as measured along the Y-axis, or between 0.25 and 0.75 inches in various embodiments. The first extension 56 and the second extension 58 may each simultaneously extend away from the center part 54 along the Y-axis and away from the body 51 along the X-axis. The edge 53 may define a concave part that opens away from the body 51. Each of the first extension 56 and the second extension 58 may have a rounded end.

Figure 12:
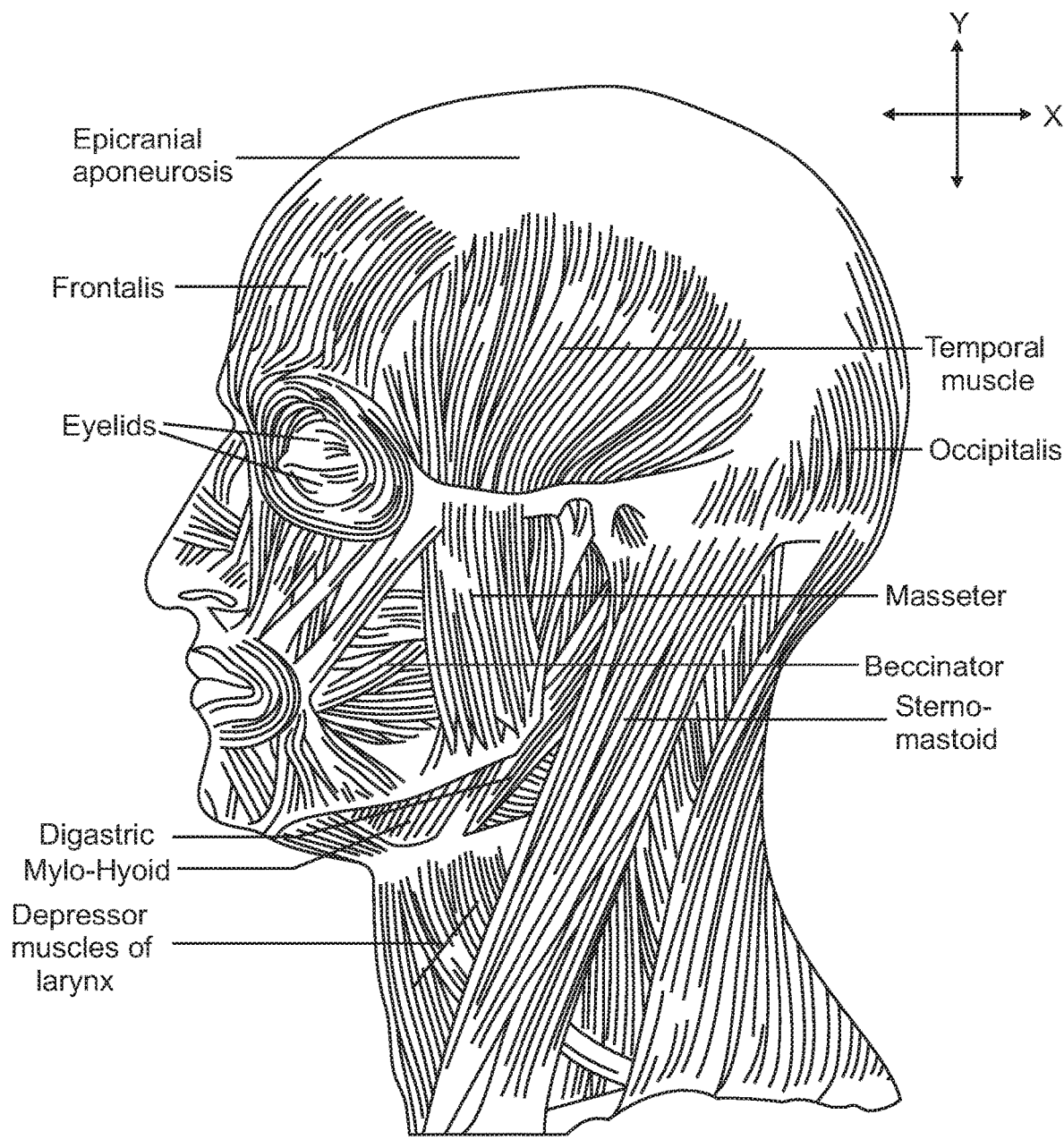
FIG. 12 is an anatomical diagram illustrating musculature of a user's head neck.

FIG. 12 illustrates a possible musculature diagram of a user that may assist with identifying where the device 10, 20, 30, 40, 50 may be placed. The devices 10, 20, 30, 40, 50 may be adhered to the skin over the sternomastoid muscle behind the user's ear, as measured along the X-axis. Portions of the device 20, 30, 40, 50 may extend over and be adhered to the skin over sternomastoid muscle below the user's ear, and in proximity to the user's digastric muscle. Portions of the device may or may not be adhered to the user's skin over the digastric muscle. A non-adhesive portion of the body 4, 21, 31 may be stretched over the user's head, and may cross over the temporal muscle and epicranial aponeurosis without crossing the occipitalis. In other embodiments, a non-adhesive portion of the body 4, 21, 31, 41, 51 may be stretched behind the user's head to cross over the occipitalis or below the occipitalis and across the back of a user's neck.

Figure 13:
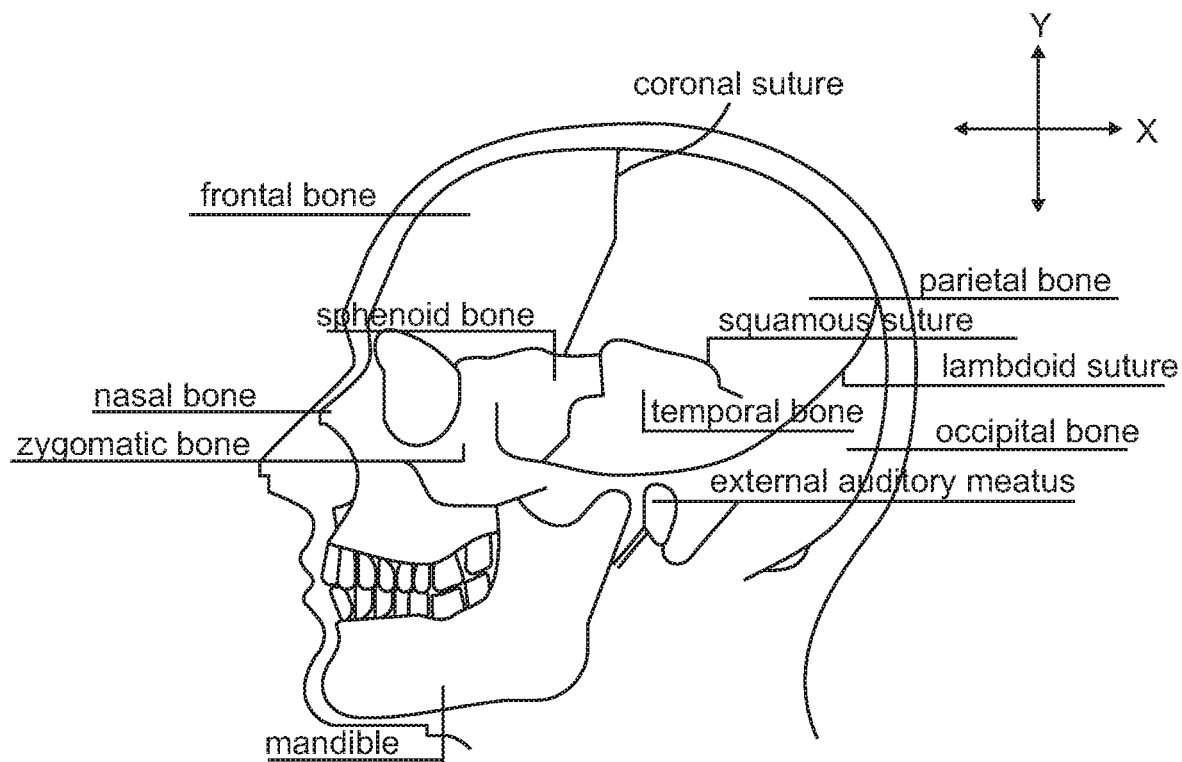
FIG. 13 is a skeletal diagram of a user's head.

FIG. 13 illustrates a possible skull anatomy diagram of a user that may also assist with identifying where the device 10, 20, 30, 40, 50 may be placed. The devices that may be worn over the head and are attached behind the ear may be adhered to the user's skin behind the external auditory meatus, as measured along the X-axis. Portions of the device 20, 30, 40, 50 may extend over and be adhered to the skin behind the external auditory meatus along the X-axis and below the external auditory meatus along the Y-axis, in proximity to the user's mandible. A non-adhesive portion of the body 4, 21, 31 may be stretched over the user's head, and may cross over the temporal bone and squamous suture without crossing the coronal suture. Portions of the parietal bone and occipital bone may or may not be crossed by the body 4, 21, 31 when stretched over and/or behind the user's head. In other embodiments, a non-adhesive portion of the body 4, 21, 31, 41, 51 may be stretched behind the user's head, crossing over or passing beneath the occipital bone without crossing the lambdoid suture.

Figure 15:
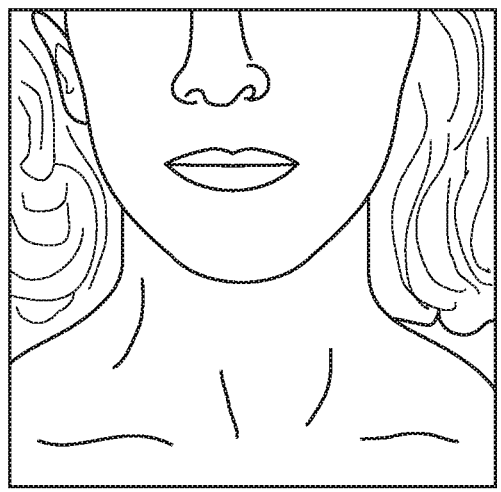
FIG. 15 illustrates another potential after view of a user's neck.

FIG. 14 illustrates possible before and after results of using the device 10, 20, 30, 40, 50, either in the over the head configuration and/or in the behind the head configuration. FIG. 15 presents an additional view of the possible after effects of using the device 10, 20, 30, 40, 50.

The device 10, 20, 30, 40, 50 may provide women (and men) with an alternative option to having a surgical neck lift procedure. Face and neck lifts can be very costly, dangerous and sometimes deadly. There may be downtime with scaring and pain and sometimes an unnatural look, and after a few years, the skin stretches again and the process may need to be repeated. Plastic surgeons may lead one to believe that surgery is the only way or only reasonable or acceptable way to achieve tightening in the neck area.

However, with the device 10, 20, 30, 40, 50, there is no downtime, no major cost, no surgery, or drugs. The device 10, 20, 30, 40, 50 may simply provide great results within approximately five minutes. One can wear or remove the device 10, 20, 30, 40, 50 anytime one chooses. The device 10, 20, 30, 40, 50 may be capable of absorbing and/or releasing moisture due to its breathability, which may assist with maintaining adhesion. The device 10, 20, 30, 40, 50 may be clean, easy, affordable, reliable and give confidence for years to come for a better and safer alternative to surgery.

When adhered to the user's head, part of each end of the device 10, 20, 30, 40, 50 may be disposed between one of the user's ears and the user's head and/or neck. Whether the device 10, 20, 30, 40, 50 is stretched over the head or behind the head, part of the device may be adhered to an area of the user's skin that is covered by a projection of the user's ear against the user's head and/or neck parallel to an axis that runs between similar points of the user's ears (e.g., from earlobe to earlobe). When used, each end of the device 10, 20, 30, 40, 50 may be abutted against and/or proximate to the rear side of the connection of the user's ear to the user's head. The above adhesion area may provide benefits for concealment, reliability of the product, and/or a lifting effect of the user's neck. For example, in FIGS. 5 and 6, the device 20 is shown to be partially concealed behind the user's ear. The device 20 may be seen to be disposed proximate to the rear side of the connection of the user's ear to the user's head, and part of the second extension 28 and the body 21 may be seen to be between the user's ear and head and/or neck. Similarly, in FIG. 9, parts of the center part 44, the first extension 46, and the second extension 48 may be seen to be between the user's ear and the user's head and/or neck.

More preferred embodiments may provide better lifting effects, and may be more easily concealed, reliable, comfortable, manufactured, lower cost, easily applied, and/or adhere longer than other embodiments. Most preferred embodiments may be better in one or more of the above aspects than more preferred embodiments.

Although the invention has been described using specific terms, devices, and/or methods, such description is for illustrative purposes of the preferred embodiments only. Changes may be made to the preferred embodiments by those of ordinary skill in the art without departing from the scope of the present invention, which is set forth in the following claims. In addition, it should be understood that aspects of the preferred embodiments generally may be interchanged in whole or in part.

What is claimed is:

1. A method for applying a device for stretching skin of a user's neck, comprising the steps of:
   obtaining a stretchable body that extends along a first axis, wherein the stretchable body is made of a urethane;
   a first end integrally connected to the stretchable body;
   a second end integrally connected to the stretchable body; and
   an adhesion layer formed on one side of each of the first end and the second end for attaching the device to the skin of the user,
   each of the first end and the second end comprising
      a center part that is integrally formed with the stretchable elongate body,
      a first extension spaced from the stretchable elongate body, the first extension being connected to the center part and extending along a second axis away from the center part, and
      a second extension spaced from the stretchable elongate body, the second extension being connected to the center part opposite the first extension and extending along the second axis away from the center part and the first extension, and wherein each of the first end and the second end further comprises
   an edge that is distal to the stretchable body, and
   a mid-line disposed approximately midway between the edge and a connecting location between the stretchable body and a corresponding one of the first end and the second end,
   each of the first extension and the second extension increasing in width, as measured along the second axis, from the connecting location to a location between the mid-line and the edge, and
   each of the first extension and the second extension remaining constant in width, as measured along the second axis, between the mid-line and the edge,
   wherein the first extension of the first end and the first extension of the second end are spaced from each other,
   wherein the second extension of the first end and the second extension of the second end are spaced from each other, and
   wherein the stretchable body is made of a urethane that is between 0.5 and 1.5 millimeters in thickness, the device is between 0.25 and two inches wide, and between six and ten inches long, and
   wherein there are further steps of:
   adhering part of the first extension of the first end of the device to an area of the user's skin behind the user's ear;
   stretching the stretchable body of the device to permit the device to be attached to different parts of the user's skin; and
   adhering part of the first extension of the second end of the device to an area of the user's skin behind the user's other ear and.

2. The method of claim 1, wherein in the step of adhering, the device is adhered to the user's skin over the sternomastoid muscle behind the user's ear at each of the first and second ends and the stretchable body is stretched over the user's head, across over the temporal muscle and epicranial aponeurosis without crossing the occipitalis or stretched behind the user's head to cross over the occipitalis or below the occipitalis and across the back of a user's neck.

3. The method of claim 1, wherein in the step of adhering, the device is adhered to the user's skin over the sternomastoid muscle below the user's ear, and in proximity to the user's digastric muscle, at each of the first and second ends and the stretchable body is stretched over the user's head, across over the temporal muscle and epicranial aponeurosis without crossing the occipitalis or stretched behind the user's head to cross over the occipitalis or below the occipitalis and across the back of a user's neck.

4. The method of claim 1, wherein in the step of adhering, portions of the device are adhered to the user's skin over the digastric muscle and the stretchable body is stretched over the user's head, across over the temporal muscle and epicranial aponeurosis without crossing the occipitalis or stretched behind the user's head to cross over the occipitalis or below the occipitalis and across the back of a user's neck.

5. A device for stretching skin of a user's neck, comprising:
   a stretchable body that extends along a first axis, wherein the stretchable body is made of a urethane;
   a first end integrally connected to the stretchable body;
   a second end integrally connected to the stretchable; and
   an adhesion layer formed on one side of each of the first end and the second end for attaching the device to the skin of the user's neck,
   each of the first end and the second end comprising
      a center part that is integrally formed with the stretchable elongate body,
      a first extension spaced from the stretchable elongate body, the first extension being connected to the center part and extending along a second axis away from the center part, and
      a second extension spaced from the stretchable elongate body, the second extension being connected to the center part opposite the first extension and extending along the second axis away from the center part and the first extension, and wherein each of the first end and the second end further comprises
   an edge that is distal to the stretchable body, and
   a mid-line disposed approximately midway between the edge and a connecting location between the stretchable body and a corresponding one of the first end and the second end,
   each of the first extension and the second extension increasing in width, as measured along the second axis, from the connecting location to a location between the mid-line and the edge and having curved edges, and
   each of the first extension and the second extension remaining constant in width, as measured along the second axis, between the mid-line and the edge,
   wherein the first extension of the first end and the first extension of the second end are spaced from each other,
   wherein the second extension of the first end and the second extension of the second end are spaced from each other, and
   wherein the stretchable body is made of a urethane that is between 0.5 and 1.5 millimeters in thickness, the force needed to overcome the tensile strength limit of the stretchable body is between 11 and 17 pounds, the device is between 0.25 and two inches wide, and between 1.5 and six inches long.

6. The device of claim 5, wherein the first extension and the second extension are configured to adhere to the user's skin to resist lifting at the edges of the end of the device caused by a narrowing of the stretchable body when placed under tension.

7. The device of claim 5, wherein the device has an upright moisture vapor transmission rate 700 and 900 $g/m^2/$ 24 hours.

8. The device of claim 5, wherein the device is configured to be adhered behind and in proximity to the user's ear before and stretched over the top of the user's head.

9. The device of claim 5, wherein the device is configured to be adhered behind and in proximity to the user's ear and stretched behind the user's head.

10. The device of claim 5, wherein the device is configured to be adhered behind and in proximity to the user's ear such that a portion of the device is disposed between the user's ear and the user's head.

11. The device of claim 5, wherein the device is configured to be adhered to an area of the user's skin that is covered by a projection of the user's ear against the user's head parallel to an axis that runs between similar points of the user's ears.

12. The device of claim 5, wherein:
   at least part of the first extension of the first end of the device is configured for being adhered to an area of the user's skin between the user's ear and the user's head,
   the stretchable body of the device is configured for being stretched to permit the device to be attached to different parts of the user's skin, and
   at least part of the first extension of the second end of the device is configured for being adhered to an area of the user's skin between the user's other ear and the user's head.

13. The device of claim 12, wherein the stretchable body of the device is configured for being stretched behind the user's head and over the user's occipitalis.

14. The device of claim 12, wherein the stretchable body of the device is configured for being stretched behind the user's head and below the user's occipitalis.

15. The device of claim 12, at least part of the first extension of the first end of the device and at least part of the first extension of the second end of the device, respectively, are configured for attachment to the skin over the sternomastoid muscle behind each of the user's ears.

16. The device of claim 5, wherein each of the first extensions and the second extensions for each of the first end and the second end are tapered at the junction of the stretchable body and the first end and at the junction of the stretchable body and the second end, respectively.

17. The device of claim 5, wherein the adhesion layer is a solvent based acrylic adhesive.

18. The device of claim 5, wherein the length of the device is between 3 and 5 inches.

19. The device of claim 5, wherein the width of the first end and the second end as measured along the second axis are each between 0.75 and 2 inches.

* * * * *